United States Patent [19]

Rei et al.

[11] Patent Number: 5,023,281

[45] Date of Patent: Jun. 11, 1991

[54] MICROBIOCIDAL COMPOSITIONS COMPRISING AN ARYL ALKANOL AND A MICROBIOCIDAL COMPOUND DISSOLVED THEREIN

[75] Inventors: Nuno M. Rei, Boxford; Ronald C. Wilson, Wenham, both of Mass.

[73] Assignee: Morton International, Inc., Chicago, Ill.

[21] Appl. No.: 383,125

[22] Filed: Jul. 20, 1989

Related U.S. Application Data

[62] Division of Ser. No. 301,691, Jan. 25, 1989, which is a division of Ser. No. 15,242, Feb. 17, 1987, which is a division of Ser. No. 619,092, Jun. 11, 1984, Pat. No. 4,663,077.

[51] Int. Cl.$^5$ ............... A01N 31/00; A01N 43/80; A61K 31/425

[52] U.S. Cl. ................... 523/122; 514/372; 514/730; 252/106; 252/364; 252/308; 424/78

[58] Field of Search ............ 523/122; 514/372, 730; 252/106, 364, 308; 424/78

[56] References Cited

U.S. PATENT DOCUMENTS

| | | | |
|---|---|---|---|
| 1,514,327 | 11/1924 | Dow et al. | 514/370 |
| 3,360,431 | 12/1967 | Yeager | 523/122 |
| 3,755,224 | 8/1973 | Lutz, Jr. | 524/114 |
| 3,890,270 | 6/1975 | Minien | 260/458 N |
| 4,446,153 | 5/1984 | Yang | 424/343 |
| 4,461,975 | 11/1983 | Green et al. | 430/327 |

FOREIGN PATENT DOCUMENTS

| | | | |
|---|---|---|---|
| 1031524 | 6/1966 | European Pat. Off. | 514/730 |
| 56-081373 | 7/1981 | Japan . | |

*Primary Examiner*—John Doll
*Assistant Examiner*—Pili Curtis
*Attorney, Agent, or Firm*—Gerald K. White; Herbert W. Larson

[57] ABSTRACT

Provided are microbiocidal solutions comprising an aryl alkanol solvent and a microbiocidal compound dissolved therein. The solutions may be used to impart microbiocidal properties to polymer compositions.

7 Claims, No Drawings

MICROBIOCIDAL COMPOSITIONS COMPRISING AN ARYL ALKANOL AND A MICROBIOCIDAL COMPOUND DISSOLVED THEREIN

This is a divisional of co-pending application Ser. No. 07/301,691 filed on Jan. 25, 1989 which is a division of Ser. No. 07/015,242 filed on Feb. 17, 1987 which is in turn a divisional of Ser. No. 619,092 filed on June 11, 1984 now U.S. 4,663,077.

BACKGROUND OF THE INVENTION

1. Field of the Invention

This invention relates to liquid microbiocidal solutions containing an aryl alkanol and a microbiocidal compound dissolved in said aryl alkanol.

This invention also relates to compositions comprising a polymer processing aid and a microbiocidal compound dissolved in an aryl alkanol.

This present invention further relates to a process for imparting microbiocidal properties to polymer compositions comprising adding to the polymer composition a liquid microbiocidal solution comprising an aryl alkanol and a microbiocidal compound dissolved therein.

This invention also relates to a process for imparting microbiocidal properties to a polymer composition comprising adding to the polymer composition a composition comprising a polymer processing aid and a microbiocidal compound which is present in the polymer processing aid as the solute in an aryl alkanol solvent.

This invention further relates to compositions comprising a solution of a liquid plasticizer for vinyl resins and a microbiocidal amount of a microbiocidal compound dissolved in an aryl alkanol.

This invention further relates to vinyl resin compositions comprising an admixture of a vinyl resin and a vinyl resin plasticizer containing, in an amount sufficient to impart microbiocidal properties to the vinyl resin composition, a microbiocidal compound dissolved in an aryl alkanol.

2. Prior Art

It is presently common practice to protect polymer or plastic compositions from microbial, e.g. bacterial or fungal, attack by incorporating a microbiocidal composition into the polymer or plastic. The resulting polymer compositions prevent the deterioration of articles formed from the polymer compositions due to microbiological attack on the plasticizers or other polymer additives which are normally incorporated into the polymer to impart desirable physical properties to the article and to facilitate forming of the article.

Many of the available microbiocidal materials are solid and, in order to incorporate them homogeneously in the polymer composition, it is necessary to first mix them with a liquid which solubilizes or disperses the material uniformly and thereafter, mix the thus-formed liquid composition with the polymer. Unfortunately, the solubility of many of the microbiologically active materials in the more common solvent materials is quite low. Therefore, it is either difficult to incorporate a sufficiently high concentration of the microbiocidal material with the polymer or, if sufficiently high concentrations of the microbiocidal material can be incorporated in the polymer, an undesirably high concentration of the solvent must also be incorporated in the polymer with the resultant deterioration of the desirable characteristics of the polymer composition.

Attempts to solve these problems have met with varying, often limited, success. For example, U.S. Pat. No. 3,288,674 issued Nov. 29, 1966 to Yeager and U.S. Pat. No. 3,689,449 issued Sept. 5, 1972 to Yeager and Wilson disclose the use of solvents having a labile hydrogen, preferably nonyl phenol, to dissolve microbiocidally active phenoxarsine compounds, the resulting solution being subsequently incorporated into resin compositions. Unfortunately, the solubility of the phenoxarsine in nonyl phenol is limited to low concentrations which necessitates incorporating nonyl phenol in the resin at higher concentrations that desirable in order to attain the desired phenoxarsine levels in the resin.

U.S. Pat. No. 3,360,431 issued Dec. 1967 to Yeager discloses the use of labile hydrogen-containing solvents, preferably nonyl phenol, to dissolve microbiocidally active arsenobenzene compounds for subsequent addition to resin compositions.

U.S. Pat. No. 4,049,822 issued Sept. 20, 1977 to Rei and Wilson discloses microbiocidal phenoxarsines dissolved in glycyl phosphites or glycyl phosphonates, the resulting solution being subsequently incorporated into resin compositions.

SUMMARY OF THE INVENTION

In accordance with the present invention there are provided liquid microbiocidal solutions comprising an aryl alkanol and a microbiocidal compound dissolved therein.

Also provided in accordance with this invention are compositions comprising a polymer processing aid and, in an amount at least sufficient to impart microbiocidal properties to the composition, a microbiocidal compound which is present in the polymer processing aid as the solute in an aryl alkanol solvent.

There is also provided in accordance with the present invention a process for imparting microbiocidal properties to a polymer composition comprising adding to the polymer composition a liquid microbiocidal solution comprising an aryl alkanol and, in an amount sufficient to impart microbiocidal properties to the polymer composition, a microbiocidal compound dissolved therein. This invention also includes the product produced by this process.

There is further provided in accordance with this invention a process for imparting microbiocidal properties to a polymer composition comprising adding to the polymer composition a composition comprising a polymer processing aid and, in an amount at least sufficient to impart microbiocidal properties to the polymer composition, a microbiocidal compound which is present in the polymer processing aid as the solute in an aryl alkanol solvent. The product of this process is also included in the invention.

There are also provided in accordance with this invention compositions capable of plasticizing vinyl resins and imparting microbiocidal properties thereto, said compositions comprising a liquid plasticizer for vinyl resins and in an amount sufficient to impart microbiocidal properties to the plasticizing composition a microbiocidal compound present in the plasticizer as the solute in an aryl alkanol solvent, said solute and solvent being a liquid uniformly distributed in said plasticizer to form a single phase system.

There are further provided in accordance with this invention vinyl resin compositions comprising an admixture of vinyl resin and a vinyl resin plasticizer, said vinyl resin composition containing, in an amount sufficient to impart microbiocidal properties to said vinyl resin composition, a microbiocidal compound present in said plasticizer as the solute in an aryl alkanol solvent.

DESCRIPTION OF THE PREFERRED EMBODIMENTS

The aryl alkanols useful as solvents in the practice of this invention are compounds which have an hydroxyl group attached to an aromatic ring through an alkylene group. That is, the aryl alkanols of this invention contain an aromatic ring to which is attached a group having the formula —R—OH where R is a straight or branched-chain alkylene group, preferably having 1–6 carbon atoms, more preferably 1–3 carbon atoms and most preferably 1 carbon atom. The alkylene group may be unsubstituted or substituted with other groups such as, for example, halogens, amines, methyl hydroxyl, or alkoxyl groups.

The term aryl as used herein refers to aromatic rings which may be substituted with functional groups. Examples of such aromatic rings include, but are not limited to, benzene, naphthalene, and biphenyl rings. When the aryl group is substituted with functional groups, it may have any number of groups attached to the aromatic ring, it being required only that the type of functional groups, their position on the ring and/or their number does not interfere with the aryl alkanol's ability to dissolve the microbiocidal compound or, if it is to be employed as part of a polymer composition, its compatibility with the polymer. Examples of such functional groups on the aryl rings include, but are not limited to, halogen, aryloxy, amino, hydroxyl, alkoxyl, and nitro groups.

The aryl alkanols useful in the practice of this invention may be further defined by the following general formula:

wherein A is an aromatic ring, preferably benzene, which may be unsubstituted, e.g. phenyl, or substituted with one or more halo, aryloxy, amino, hydroxyl, alkoxyl or nitro groups; and R is a straight or branched chain alkylene group, preferably having 1–6 carbon atoms, which may be unsubstituted or substituted with halo, amino, methyl, hydroxyl or alkoxyl groups.

The aryl alkanols which are useful in the practice of the present invention are those in which the hydroxyl group of the alkanol is a primary, secondary or tertiary alcohol. The preferred aryl aklanols are those in which the hydroxy group is a primary alcohol.

Examples of aryl alcohols which may be employed in accordance with this invention include, but are not limited to, the following:

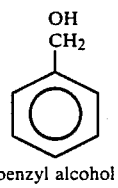

benzyl alcohol

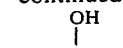

styralyl alcohol
(methyl benzyl alcohol)

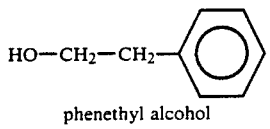

phenethyl alcohol

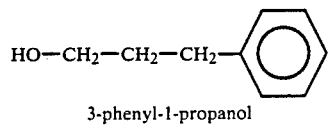

3-phenyl-1-propanol

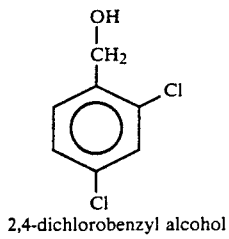

2,4-dichlorobenzyl alcohol

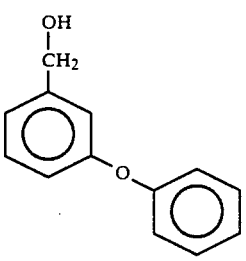

m-phenoxy benzyl alcohol

Of these aryl alkanols, benzyl alcohol, 2, 4-dichlorobenzyl alcohol, and styralyl alcohol are preferred, benzyl alcohol being especially preferred.

The aryl alkanols exemplified above are all liquids with the exception of 2,4-dichlorobenzyl alcohol, which is a solid. This compound has quite surprisingly been found to act as a solvent (or co-solvent) for those microbiocidal compounds which are liquids. If the 2,4-dichlorobenzyl alcohol is heated slightly it melts and then can be combined with the liquid microbiocidal compound to form a stable solution. The 2,4-dichlorobenzyl alcohol also exhibits microbiocidal activity by itself. Thus, it can be dissolved in another aryl alkanol, for example benzyl alcohol, to produce a microbiocidal solution in accordance with this invention.

A wide variety of microbiocidal compounds are useful in the practice of this invention. In general, the useful microbiocidal compounds possess microbiocidal activity and are soluble in an aryl alkanol. If the aryl alkanol/microbiocidal compound solution is to be employed in compositions containing polymer processing aids and/or polymers, the microbiocidal compound should be compatible with such processing aids or polymers.

Examples of the types of microbiocidal compounds which may be employed in this invention include, but are not limited to, phenoxarsines(including bisphenoxarsines), phenarsazines (including bisphenarsazines), maleimides, isoindole dicarboximides, having a sulfur atom bonded to the nitrogen atom of the dicarboximide group, halogenated aryl alkanols and isothiazolinone compounds.

The microbiocidal phenoxarsine and phenarsazine compounds useful in the compositions of this invention include compounds represented by the formulas:

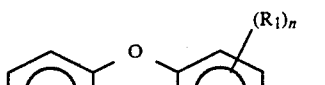

and

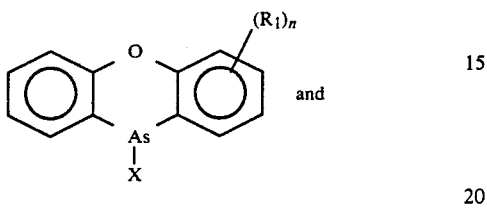

where X is halogen or thiocyanate, Y is oxygen or sulfur, Z is oxygen or nitrogen, R is halo or lower alkyl, and n is 0 to 3. Examples of these phenoxarsines and phenarsazines include, but are not limited to, 10-chlorophenoxarsine; 10-iodophenoxarsine; 10-bromophenoxarsine; 4-methyl-10-chlorophenoxarsine; 2-tert-butyl-10-chlorophenoxarsine; 1, 4-dimethyl-10chlorophenoxarsine; 2-methyl-8, 10-dichlorophenoxarsine; 1, 3, 10-trichlorophenoxarsine; 2, 6, 10-trichlorophenoxarsine; 1, 2, 4, 10-tetrachlorophenoxarsine; 10, 10′-oxybisphenoxarsine (OBPA); 10-thiocyanato phenoxarsine; and 10, 10′-thiobisphenoxarsine; 10,10′-oxybisphenarsazine and 10,10′-thiobisphenarsazine.

The microbiocidal maleimide compounds useful in the compositions of this invention are exemplified by a preferred maleimide, N-(2-methylnaphthyl) maleimide.

The microbiocidal compounds useful in the practice of this invention which are isoindole dicarboximides having a sulfur atom bonded to the nitrogen atom of the dicarboximide group are compounds which contain at least one group having the structure:

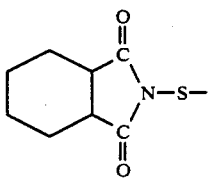

The preferred isoindole dicarboximides are the following:

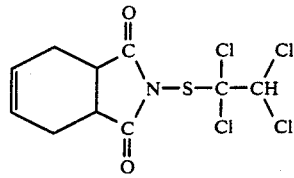

bis-N-[(1,1,2,2-tetrachloroethyl)thio]-4-cyclohexene-1, 2-dicarboximide

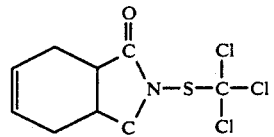

N-trichloromethylthio-4-cyclohexene-1,2-dicarboximide

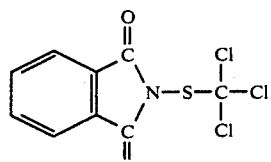

N-trichloromethylthio phthalimide

The halogenated aryl alkanols which can be used as microbiocidal compounds in accordance with this invention are exemplified by a preferred compound, 2, 4-dichlorobenzyl alcohol.

An example of a preferred isothiazolinone compound useful in the composition of this invention is 2-(n-octyl-4-isothiazolin-3-one).

The most preferred microbiocidal compounds are the bisphenoxarsines and bisphenarsazines having the formula:

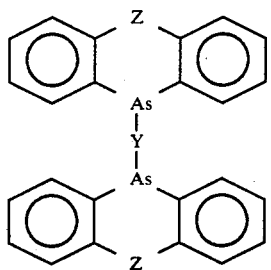

where Y is oxygen or sulfur and Z is oxygen or nitrogen. Of those bisphenoxarsines and bisphenarsazines, the most preferred are 10, 10′-oxybisphenoxarsine; 10, 10′-thiobisphenoxarsine; 10, 10′-oxybisphenarsazine; and 10, 10′-thiobisphenarsazine.

The microbiocidal compositions useful in this invention should be employed in an amount at least sufficient to impart microbiocidal properties to the composition or material containing them. This amount can vary widely depending upon the particular microbiocidal compound employed, the other components of the composition in which it is employed, the environment in which it will function and several other factors. The minimum amount of microbiocidal compound employed will be determined by what is known in the art as its Minimum Inhibitory Concentration (MIC). The maximum amount of microbiocidal compound which can be employed is determined only by the amount of microbiocidal compound which can be uniformly incorporated into a particular composition without adversely affecting the physical properties of the composition. In general, the compositions of this invention which possess microbiocidal properties contain from about 50 parts per million (ppm) to about 10,000 ppm, preferably about 100 ppm to 500 ppm, of microbiocidal compound.

The liquid microbiocidal solutions of this invention preferably contain much more microbiocidal compound than would be necessary simply to impart the desired microbiocidal properties to them. This is also true for the polymer processing aid-containing composition. These compositions can contain large amounts of microbiocidal compound since they are advantageously employed as "concentrates" to produce compositions which have a lower concentration of microbiocidal compound, but still have the desired degree of microbiocidal activity. For example, the liquid microbiocidal solutions may contain from about 0.1 to about 30 weight percent microbiocidal compound (based on total solution weight). However, a solution containing, for example, 25% microbiocidal compound may be used to prepare a polymer processing aid-containing composition which contains only about 5% microbiocidal compound, which polymer processing aid-containing composition may in turn be used to prepare a polymer composition containing only 100 to 500 ppm microbiocidal compound.

The microbiocidal solutions of this invention may be employed as additives for polymer compositions to impart microbiocidal properties to said polymer compositions. They may be added either directly to the polymer composition or they may be first incorporated into a polymer processing aid which serves as a carrier for incorporating the microbiocidal solutions into the polymer composition. When the latter manner is chosen, the polymer processing aids may be any of a variety of materials which are compatible with the polymer composition and microbiocidal solution (e.g. the microbiocidal compound does not precipitate or otherwise separate from the composition solution when used with the processing aid). Examples of these polymer processing aids include, but are not limited to, plasticizers, lubricants, and volatile and non-volatile solvents. Specific examples of these processing aids include, but are not limited to, typical plasticizers such as tricresyl phosphate, dipropylene glycol dibenzoate, diphenylcresyl phosphate, dipropylene glycol dibenzoate, diphenylcresyl phosphate, epoxidized soya, epoxidized tallate, dioctyl azelate, di(2-ethyl hexyl) phthalate, alkyl aryl phosphates, diisobutyl phthalate, diisodecyl phthalate, hydrogenated methyl rosin ester, n-octyl n-decyl phthalate, mixed n-alkyl phthalates, butyl benzyl phthalate, di-n-octyl phthalate, di-n-decyl phthalate, 3,4-epoxycyclohexyl methyl 3,4-epoxycyclohexane carboxylate, trioctyl trimellitate and low molecular weight polymeric plasticizers such as Paraplex G-30 plasticizer sold by Rohm & Haas Co. and the like. Of those plasticizers, di(2-ethyl hexyl) phthalate, diisodecyl phthalate, butyl benzyl phthalate and epoxidized soya are preferred. Other polymer processing aids useful in this invention include, but are not limited to, polypropylene glycol; 1,4-butanediol; silicone oils such as polydimethylsiloxane; and methyl ethyl ketone.

As previously indicated, the concentration of microbiocidal compound in the microbiocidal solution may be sufficiently high that the polymer processing aid-containing composition prepared from said microbiocidal solution will in turn contain enough micro-biocidal compound that, when the polymer processing aid-containing composition is added to a polymer, the ultimately-formed polymer composition and articles prepared therefrom will have microbiocidal properties. It is in this aspect of the invention where the solvents employed in the practice of the present invention are particularly advantageous. The aryl alkanols of this invention are capable of forming microbiocidal solutions which will produce polymer processing aid-containing compositions containing concentrations of microbiocidal compounds significantly higher than could be achieved with prior art solvents. For example, heretofore OBPA-containing plasticizing compositions contained a maximum of about 2% by weight OBPA based on the weight of the plasticizing composition. It has now been quite unexpectedly found that the aryl alkanols of this invention are capable of producing OBPA-containing plasticizing compositions containing at least 5% by weight OBPA based on the weight of the plasticizing composition.

This unexpected ability of the aryl alkanols to produce polymer processing aid-containing compositions containing high levels of microbiocidal compound leads to several very significant advantages. For example, shipping and handling cost savings are achieved because more "active ingredient" (the microbiocidal compound) can now be dissolved in a given amount of polymer processing aid-containing composition. Stated another way, for a given amount of microbiocidal compound, less "inert ingredients" (solvent and polymer processing aid) are required to produce a polymer processing aid-containing composition, resulting in raw material cost savings. Also, because less inert ingredients are needed, handling and shipping costs are lower.

The polymer processing aid-containing compositions of this invention also minimize the potential effects of the solvent for the microbiocidal compounds on polymer formulations containing them. Because less solvent is required to prepare a polymer processing aid-containing composition containing a given level of microbiocidal compound, less solvent is introduced into the polymer formulatior. Therefore, if the solvent is not entirely compatible with the other components of the polymer formulation, the negative effects of that incompatibility will be minimized.

Apart from their ability to dissolve more microbiocidal compound, the aryl alkanols of this invention also have the surprising advatage of producing polymer processing aid-containing compositions which are low in odor and less irritating compared to the solvents disclosed in the prior art such as nonyl phenol and phosphites.

It has also been quite surprisingly discovered that the microbiocidal solutions of the present invention can often be prepared at temperatures considerably lower than those required with the solvents of the prior art. For example, in order for nonyl phenol to dissolve OBPA, a nonyl phenol/OBPA mixture must generally be heated to about 300° F. However, a benzyl alcohol/OBPA, solution according to the present invention may be prepared by heating to only about 140° F. Obviously, when large masses of material are required to be heated, as in a commercial operation, the lower temperature requirement of the microbiocidal solutions of this invention can result in tremendous energy savings. The lower temperature also helps prevent undesirable chemical reactions (such as the oxidation of benzyl alcohol to benzaldehyde) from occurring.

The polymers employed in the processes and products of this invention cover a wide variety of materials. In general, they include thermoplastic and thermosetting polymers, elastomers and other materials commonly known as "plastics". Other organic materials, for instance naturally occurring materials such as natural rubbers, cellulose and the like are considered full equivalents of the "polymers" of this invention and should be included within that term. Examples of the polymers useful in the practice of this invention include, but are not limited to vinyl resins (such as those made from vinyl chloride and/or vinyl esters) polyolefins (such as polyethylene and polypropylene), elastomeric polyurethanes, nylon, polystyrene, polyesters (such as polyethylene terephthalate), polycarbonates, acrylonitrile-butadiene-styrene (ABS) copolymers, SBR rubbers, styrene-acrylonitrile copolymers, acrylic polymers, thermosetting polyurethanes (such as those used for foams and coatings), phenolic resins, silicone rubbers, natural rubber, EDPM polymers, cellulose and its derivatives, epoxy resins and various latexes.

The microbiocidal solutions of this invention can be prepared by simply adding the desired amount of microbiocidal compound to the aryl alkanol solvent, heating the resulting mixture to a temperature which will cause the microbiocidal compound to dissolve, and maintaining that temperature until all of the microbiocidal compound dissolves. The resulting solution can then be cooled to room temperature. In this manner, stable microbiocidal solutions, i.e. those wherein no significant amount of microbiocidal compound precipitates from the solution upon cooling to room temperature, can be formed containing up to about 30% by weight microbiocidal compound based on the weight of the resulting microbiocidal solution.

The polymer processing aid-containing compositions of the present invention may be prepared by merely adding the polymer processing aid to a microbiocidal solution prepared as described above and mixing at room temperature until a uniform solution results. Alternatively, all ingredients of the polymer processing aid-containing composition (microbiocidal compound, aryl alkanol and polymer processing aid) can be mixed together and heated until the microbiocidal compound dissolves.

The microbiocidal solutions of this invention can be used to impart microbiocidal properties to polymer compositions. This can be done by simply adding the microbiocidal solution, either alone or as part of a polymer processing aid-containing composition, to the polymer composition by any of several convenient methods known in the art. Thus, for instance, the polymer composition can be melted and the microbiocidal solution or polymer processing aid-containing composition added to and mixed with it (as in an extruder). Alternatively, the polymer can be softened with or dissolved in a solvent and the microbiocidal solution or polymer processing aid-containing composition added to and mixed therewith.

The following examples illustrate the present invention, and are not intended to limit the invention or its scope in any manner. As used in the examples and throughout this specification, all parts and percentages are by weight unless otherwise indicated.

EXAMPLE 1

Several microbiocidal solutions were prepared by mixing the microbiocidal compounds and solvents indicated in Table I and heating the resulting mixtures at the temperatures indicated in Table I until they became clear. (The numbers in parentheses indicate the weight percent of each ingredient based on solution weight). The resulting clear solutions were then cooled to room temperature and aged at room temperature (RT) for varying periods of time, after which they were examined to determine whether the microbiocidal compound was still in solution.

EXAMPLE 2

Polymer processing aid-containing compositions were prepared by first preparing a solution of microbiocidal compound in an aryl alkanol solvent as described in the foregoing examples, blending the thus-formed solution with a polymer processing aid and heating the blend while stirring until thoroughly mixed. Several polymer processing aid-containing compositions were prepared in this manner using the ingredients and conditions indicated in Table II with the results also indicated in Table II. All percentages in Table II are by weight percent based on the total weight of the compositions.

TABLE I

| SOLUTION NO. | MICROBIOCIDAL COMPOUND | SOLVENT | TEMP. (°C.) | RT | SOLUBILITY[5] AFTER 24 HOURS RT | AFTER 7 DAYS RT | AFTER 1 MO. RT |
|---|---|---|---|---|---|---|---|
| | | | (93° C.) | | | | |
| F | OBPA (28.6%) | benzyl alcohol (71.4%) | S | S | — | S | — |
| K | OBPA (27.0%) | benzyl alcohol (73.0%) | S | S | — | S | — |
| I | OBPA (25.0%) | benzyl alcohol (75.0%) | S | S | — | S | — |
| J | OBPA (20.0%) | benzyl alcohol (80.0%) | S | S | — | S | — |
| | | | (71-104° C.) | | | | |
| 1 | OBPA (20.0%) | styralyl alcohol (80.0%) | S | S | S | — | MP |
| 2 | OBPA (20.0%) | phenethyl alcohol (80.0%) | S | S | S | — | S |
| 3 | OBPA (20.0%) | 3-phenyl-1-propanol (80.0%) | S | S | S | — | S |
| 5 | OBPA (20.0%) | m-phenoxy benzyl alcohol (80.0%) | S | S | S | — | S |
| 7 | OBPA (20.0%) | benzyl alcohol | S | S | S | — | S |

TABLE I-continued

| SOLUTION NO. | MICROBIOCIDAL COMPOUND | SOLVENT | TEMP. (°C.) | RT | SOLUBILITY[5] AFTER 24 HOURS RT | AFTER 7 DAYS RT | AFTER 1 MO. RT |
|---|---|---|---|---|---|---|---|
| A | RH-893[1] (10.0%) | (80.0%) benzyl alcohol (90.0%) | S | S | S | S | — |
| B | ATV-129[2] (10.0%) | benzyl alcohol (90.0%) | S | S | SP | SP | — |
| C | Myacide SP[3] (10.0%) | benzyl alcohol (90.0%) | S | S | S | S | — |
| D | Vancide 89[4] (10.0%) | benzyl alcohol (90.0%) | S | S | SP | SP | — |
| H | OBPA (10.0%) | benzyl alcohol (90.0%) | S | S | S | S | — |

[1] 2-(n-octyl)-4-isothiazolin-3-one
[2] N-(2-methyl-1-naphthyl) maleimide
[3] 2,4-dichlorobenzyl alcohol
[4] N-trichloromethyl thio-4-cyclohexene-1,2-dicarboximide
[5]
S = soluble
SP = slight precipitate
MP = medium precipitate

TABLE II

| COMP. NO. | MICROBIOCIDAL COMPOUND (%) | SOL-VENT | PLASTI-CIZER (%) | HEATED AT (°C.) | % MICROB. CMPD. IN PLAST. COMP'N | HOT | RT | SOLUBILITY AFTER 24 HRS RT | AFTER 7 DAYS RT | AFTER 1 MO. RT |
|---|---|---|---|---|---|---|---|---|---|---|
| V-11 (Control) | OBPA | None | DIDP[6] | 104° C. | 5% | S | S | HP[9] | HP | HP |
| V-1 | Sol'n 1-Table I | | DISP[6] | 104° C. | 5% | S | S | S | S | SP |
| V-2 | Sol'n 2-Table I | | " | " | 5% | S | S | S | S | S |
| V-3 | Sol'n 3-Table I | | " | " | 5% | S | S | S | S | S |
| V-5 | Sol'n 5-Table I | | " | " | 5% | S | S | S | S | S |
| V-7 | Sol'n 7-Table I | | " | " | 5% | S | S | S | S | S |
| 58 | Sol'n J-Table I | | DOP[7] | RT | 5% | S | S | — | S | — |
| 59 | Sol'n J-Table I | | DIDP | " | 5% | S | S | — | S | — |
| 60 | Sol'n J-Table I | | ESO[8] | " | 5% | S | S | — | S | — |
| 61 | Sol'n J-Table I | | DOP | " | 4% | S | S | — | S | — |
| 62 | Sol'n J-Table I | | DIDP | " | 4% | S | S | — | S | — |
| 63 | Sol'n J-Table I | | ESO | " | 4% | S | S | — | S | — |
| 64 | Sol'n I-Table I | | DOP | " | 5% | S | S | — | S | — |
| 65 | Sol'n I-Table I | | DIDP | " | 5% | S | S | — | S | — |
| 66 | Sol'n I-Table I | | ESO | " | 5% | S | S | — | S | — |
| 67 | Sol'n I-Table I | | DOP | " | 4% | S | S | — | S | — |
| 68 | Sol'n I-Table I | | DIDP | " | 4% | S | S | — | S | — |
| 69 | Sol'n I-Table I | | ESO | " | 4% | S | S | — | S | — |
| 70 | Sol'n F-Table I | | DOP | " | 5% | S | S | — | S | — |
| 71 | Sol'n F-Table I | | DIDP | " | 5% | S | S | — | S | — |
| 72 | Sol'n F-Table I | | ESO | " | 5% | S | S | — | S | — |
| 73 | Sol'n F-Table I | | DOP | " | 4% | S | S | — | S | — |
| 74 | Sol'n F-Table I | | DIDP | " | 4% | S | S | — | S | — |
| 75 | Sol'n F-Table I | | ESO | " | 4% | S | S | — | S | — |
| 76 | Sol'n K-Table I | | DOP | " | 5% | S | S | — | S | — |
| 77 | Sol'n K-Table I | | DIOP | " | 5% | S | S | — | S | — |
| 78 | Sol'n K-Table I | | ESO | " | 5% | S | S | — | S | — |
| W-1A | OBPA(1.0%) BA[19](2.0%) | | ESO (97%) | 49° C. | 1% | S | S | — | — | — |
| W-1B | OBPA(1.0%) BA[19](2.0%) | | DOP (97%) | " | 1% | S | S | — | — | — |
| W-1C | OBPA(1.0%) BA[19](2.0%) | | ODP[10] (97%) | " | 1% | S | S | — | — | — |
| W-2A | OBPA(1.0%) BA(4%) | | ESO (95%) | " | 1% | S | S | — | — | — |
| W-2B | OBPA(1.0%) BA(4%) | | DOP (95%) | " | 1% | S | S | — | — | — |
| W-2C | OBPA(1.0%) BA(4%) | | ODP (95%) | " | 1% | S | S | — | — | — |
| W-2D | OBPA(1.0%) BA(4%) | | MAP[11] (95%) | " | 1% | S | S | — | — | — |
| W-3 | OBPA(2.0%) BA(8.0%) | | ESO (90%) | " | 2% | S | S | — | — | — |
| W-4 | OBPA(2.0%) BA(8.0%) | | DOP (90%) | " | 2% | S | S | — | — | — |
| W-5 | OBPA(2.0%) BA(8.0%) | | DIDP (90%) | " | 2% | S | S | — | — | — |
| W-6 | OBPA(3.0%) BA(12.0%) | | ESO (85%) | " | 3% | SP | SP | — | — | — |
| W-7 | OBPA(3.0%) BA(12.0%) | | DOP (85%) | " | 3% | SP | SP | — | — | — |
| W-8 | OBPA(3.0%) BA(12.0%) | | DIDP (85%) | " | 3% | SP | SP | — | — | — |
| W-9 | OBPA(1.0%) BA(5.0%) | | ESO (94%) | 149° C. | 1% | S | S | — | — | — |
| W-10 | OBPA(1.0%) BA(5.0%) | | DOP (94%) | " | 1% | SP | S | — | — | SP |
| W-11 | OBPA(1.0%) BA(5.0%) | | DIDP (94%) | " | 1% | SP | S | — | — | SP |
| W-12 | OBPA(2.0%) BA(5.0%) | | ESO (93%) | " | 2% | SP | S | S | — | MP |
| W-13 | OBPA(2.0%) BA(5.0%) | | DOP (93%) | " | 2% | SP | S | — | — | MP |
| W-14 | OBPA(2.0%) BA(5.0%) | | DIDP (93%) | " | 2% | SP | S | — | — | MP |
| W-15 | OBPA(1.0%) BA(4.0%) | | DOZ[12] (95%) | " | 1% | S | S | — | — | S |
| W-16 | OBPA(1.0%) BA(4.0%) | | LT[13] (95%) | " | 1% | S | S | — | — | S |
| W-17 | OBPA(2.0%) BA(8.0%) | | DOZ (90%) | " | 2% | S | S | — | — | S |
| W-18 | OBPA(2.0%) BA(8.0%) | | LT (90%) | " | 2% | S | S | — | — | S |
| W-19 | OBPA(3.0%) BA(12.0%) | | DOZ (85%) | " | 3% | S | S | — | — | S |

TABLE II-continued

| COMP. NO. | MICROBIOCIDAL COMPOUND (%) | SOL-VENT | PLASTI-CIZER (%) | HEATED AT (°C.) | % MICROB. CMPD. IN PLAST. COMP'N | HOT | RT | SOLUBILITY AFTER 24 HRS RT | AFTER 7 DAYS RT | AFTER 1 MO. RT |
|---|---|---|---|---|---|---|---|---|---|---|
| W-20 | OBPA(3.0%) BA(12.0%) | | LT (85%) | " | 3% | S | S | — | — | S |
| W-21 | OBPA(1.0%) BA(2.0%) | | DIDP (97%) | " | 1% | S | S | — | — | S |
| W-22 | OBPA(1.03%) BA(1.5%) | | DOP (97.47%) | " | 1.03% | S | S | — | — | S |
| W-23 | OBPA(1.03%) BA(1.0%) | | DOP (97.97%) | " | 1.03% | S | S | — | — | S |
| W-24 | OBPA(1.03%) BA(0.5%) | | DOP (98.47%) | " | 1.03% | S | S | — | — | S |
| W-25 | OBPA(2.06%) BA(2.0%) | | DOP (95.94%) | " | 2.06% | S | S | — | — | S |
| W-26 | OBPA(3.09%) BA(3.0%) | | DOP (93.91%) | " | 3.09% | S | S | — | — | S |
| W-27 | OBPA(4.12%) BA(4.0%) | | DOP (91.88%) | " | 4.12% | S | S | — | — | S |
| W-28 | OBPA(1.03%) BA(2.0%) | | DIDP (96.97%) | " | 1.03% | S | S | — | — | S |
| W-29 | OBPA(1.03%) BA(1.5%) | | DIDP (97.47%) | " | 1.03% | S | S | — | — | S |
| W-30 | OBPA(1.03%) BA(1.0%) | | DIDP (97.97%) | " | 1.03% | S | S | — | — | S |
| W-31 | OBPA(1.03%) BA(0.5%) | | DIDP (98.47%) | " | 1.03% | S | S | — | — | S |
| W-32 | OBPA(2.06%) BA(2.0%) | | DIDP (95.94%) | " | 2.06% | S | S | — | — | S |
| W-33 | OBPA(3.09%) BA(3.0%) | | DIDP (93.91%) | " | 3.08% | S | S | — | — | S |
| W-34 | OBPA(4.12%) BA(4.0%) | | DIDP (91.88%) | " | 4.12% | S | S | — | — | S |
| W-35 | OBPA(3.09%) BA(3.0%) | | ESO (93.91%) | " | 3.09% | S | S | — | — | S |
| W-36 | OBPA(4.12%) BA(4.0%) | | ESO (91.88%) | " | 4.12% | S | S | — | — | S |
| W-37 | OBPA(2.06) BA(8.0%) | | G-30[14] (89.94%) | " | 2.06% | S | S | — | — | S |
| W-38 | OBPA(2.06%) BA(8.0%) | | Erla[15] (89.94%) | " | 2.06% | S | S | — | — | S |
| W-39 | OBPA(2.06%) BA(8.0%) | | TOTM[16] (89.94%) | " | 2.06% | S | S | — | — | S |
| W-40 | OBPA(2.06%) BA(8.0%) | | DOZ (89.94%) | " | 2.06% | S | S | — | — | S |
| W-41 | OBPA(2.06%) BA(8.0%) | | BBP[17] (89.94%) | " | 2.06% | S | S | — | — | S |
| W-42 | OBPA(2.0%) BA(8.0%) | | DODP[18] (90%) | " | 2.0% | S | S | — | — | S |
| W-43 | OBPA(2.06%) BA(4.0%) | | ESO (93.94%) | 116° C. | 2.06% | S | S | — | — | S |
| W-44 | OBPA(2.06%) BA(3.0%) | | ESO (94.94%) | 127° C. | 2.06% | S | S | — | — | S |
| W-45 | OBPA(2.05%) BA(1.0%) | | ESO (96.94%) | 149° C. | 2.06% | S | S | — | — | S |

[6]DIDP is diisodecyl phthalate
[7]DOP is di(2-ethyl hexyl) phthalate
[8]ESO is epoxidized soya
[9]Heavy precipitate
[10]ODP is n-octyl n-decyl phthalate
[11]MAP is mixed n-alkyl 6–10 phthalate
[12]DOZ is dioctyl azelate
[13]LT is Plastolein 9066 Lt. low temp. plasticizer sold by Emery Industries, Inc.
[14]G-30 is Paraplex. G-30 low mol. wt. polymeric plasticizer sold by Rohm & Haas Co.
[15]Erla is 3,4-epoxycyclohexyl methyl 3,4-epoxycyclohexane carboxylate
[16]TOTM is trioctyltrimellitate
[17]BBP is butyl benzyl phthalate sold as Santicizer S-160 by Monsanto Industrial Chemicals Co.
[18]DODP is di-n-octyl n-decyl phthalate sold as Santicizer 711 by Monsanto Industrial Chemicals Co.
[19]BA is benzyl alcohol

EXAMPLE 3

Several of the compositions shown in Table I and Table II were subjected to aging (storage stability) tests by aging the sample at room temperature for seven days, after which they were subjected to five freeze-thaw cycles. Each freeze-thaw (F-T) cycle consisted of storing the sample in a freezer at 0° F. for two days followed by one day at room temperature. After five of these cycles the samples were examined for stability with the following results:

TABLE III

| Solution or Plasticizing Comp'n No. | Stability after 7 days RT | Stability after 5 F-T cycles |
|---|---|---|
| F | Stable | Not Stable |
| K | Stable | Not Stable |
| I | Stable | Not Stable |
| J | Stable | Not Stable |
| 58 thru 78 | Stable | Stable |

It should be emphasized that those compositions in Table III which were not stable after the F-T cycles are still quite useful in the practice of this invention. For instance, they can be used to prepare polymer processing aid-containing compositions which are stable after F-T cycles, or can be stored and used under conditions which avoid F-T cycles.

EXAMPLE 4

Compositions W-1A through W-45 from Table II were also subjected to heat stability tests by adding the composition to a poly (vinyl chloride) plastisol in an amount such that the resulting composition contained 5% by weight plasticizing composition, and forming a film from the resulting composition. This film was then divided into several samples and placed in an oven at about 177° C. Samples were then removed from the oven at five minute intervals for 40 minutes and examined for heat stability. All of the films tested were heat stable.

EXAMPLE 5

A typical plasticizing composition according to this invention was tested to determine whether the aryl alkanol solvent contained therein had any adverse effect when the plasticizing composition is employed in a vinyl resin. The plasticizing composition was prepared by heating the following ingredients to about 160° C.

| PLASTICIZING COMPOSITION | |
|---|---|
| INGREDIENTS | WT % |
| OBPA | 3.41 |
| Benzyl alcohol | 5.50 |
| DIDP plasticizer | 91.09 |

This plasticizing composition was incorporated into a typical plasticized poly (vinyl chloride) dry blend formulation which contained the following.

| PVC DRY BLEND FORMULATION | |
|---|---|
| INGREDIENT | AMOUNT (gms) |
| PVC | 1500.0 |
| DOP plasticizer | 600.0 |
| Heat stabilizer | 90.0 |
| Stearic acid lubricant | 3.75 |
| Total | 2,193.75 gms |

The plasticizing composition was used in an amount so that the OBPA was present in the PVC dry blend formulation at the recommended level of about 500 parts per million. The resulting PVC dry blend containing the plasticizing composition was processed on a two-roll mill for approximately 15 minutes at about 163° C. During this time, the molten plastic was observed for heat stability, processing characteristics, excessive fuming of the benzyl alcohol, and irritation to the mill operator. No unusual processing difficulties, such as sticking to the mill or failure to flux or form a sheet on the hot rollers, were observed. The formulation showed no signs of degradation or excessive fuming. No irritation or odor was observed during processing. Thus, this example demonstrates that benzyl alcohol does not adversely affect the processing of typical plastic materials.

EXAMPLE 6

Antimicrobial efficacy was tested by preparing PVC films as described in Example 5 which contained a polymer processing aid-containing composition according to this invention which contained the following ingredients:

| PLASTICIZING COMPOSITION | |
|---|---|
| INGREDIENT | WT % |
| OBPA | 3.41 |
| Benzyl alcohol | 5.50 |
| DIDP | 91.09 |

A control was also made in like manner, except that it contained no antimicrobial compound.

Round samples (1 inch diameter) were cut from the PVC film samples. These round samples were then placed on a glass plate or petri dish which was previously coated with agar, innoculated with the test microorganism, and placed in an incubator under conditions and for a period of time which would normally permit the microorganism to grow on untreated agar. The dish or plate was then removed and examined for growth of the microorganism on the PVC sample.

The results of the above tests are summarized below. The term "Zone of Inhibition" refers the width of an area (measured in millimeters) around the round PVC sample in which no microorganism growth occurred on the agar. The "Growth" or "Stain" observations refer to the presence of microorganism growth or stain on the round sample (also called the "contact area").

| ZONE OF INHIBITION (mm)/GROWTH FOR STAPH. AUREUS | |
|---|---|
| SAMPLE | |
| With plasticizing composition | 8/NGCA |
| Control | 0/GCA |
| ZONE OF INHIBITION (mm)/GROWTH FOR K. PNEUMONIAE | |
| SAMPLE | |
| With plasticizing composition | 4/NGCA |
| Control | 0/GCA |
| ZONE OF INHIBITION (mm)/STAIN FOR PINK STAIN | |
| SAMPLE | |
| With plasticizing composition | 6/NS |
| Control | 0/HS |
| ZONE OF INHIBITION (mm)/GROWTH FOR MIXED FUNGAL SPORE | |
| SAMPLE | |
| With plasticizing composition | 15/NG |
| Control | 0/TG |

NGCA = No Growth in Contact Area
GCA = Growth in Contact Area
NS = No Stain
MS = Moderate Stain
HS = Heavy Stain
NG = No Growth
TG = Trace Growth
LG = Light Growth The above data shows that the polymer processing aid-containing composition is effective in preventing the growth of microorganisms on the PVC film.

We claim:

1. A composition for incorporation into a polymer comprising a plasticizer for the polymer and, in an amount at least sufficient to impart microbiocidal properties to the composition, a microbiocidal compound which is present in the composition as the solute in an aryl alkanol solvent, said microbiocidal compound being selected from the group consisting of N-(2-methylnaphthyl) maleimide, isoinodole dicarboximide having a sulfur atom bonded to the nitrogen atom of the dicarboximide group and isothiazolinone compounds.

2. A composition according to claim 1 wherein the plasticizer is selected from the group consisting of di(2-ethyl hexyl) phthalate, diisodecyl phthalate, butyl benzl phthalate and epoxidized soya.

3. A composition according to claim 1 wherein the aryl alkanol is benzyl alcohol.

4. A composition according to claim 1 which comprises at least about 2% by weight, based on the total weight of the composition, of a microbiocidal compound.

5. A composition according to claim 1 which comprises at least about 5% by weight, based on the total weight of the composition, of a microbiocidal compound.

6. A composition according to claim 1 which comprises about 50 ppm to about 10,000 ppm microbiocidal compound.

7. A composition according to claim 1 wherein the microbiocidal compound is selected from the group consisting of
N-(2-methylnaphthyl) maleimide;
bis-N-[1,1,2,2-tetrachloroethyl)thio]-4-cyclohexene-1,2-dicarboximide
N-trichloromethylthio-4-cyclohexene-1,2-dicarboximide;
N-trichloromethylthio phthalimide; and
2-(n-octyl-4-isothiazolin-3-one).

* * * * *